United States Patent
Ekstedt et al.

(10) Patent No.: US 11,857,399 B2
(45) Date of Patent: Jan. 2, 2024

(54) METHOD FOR TRANSFERRING ONE OR MORE CUT-OUT NONWOVEN MATERIAL MEMBERS FOR USE IN AN ABSORBENT ARTICLE

(71) Applicant: Essity Hygiene and Health Aktiebolag, Gothenburg (SE)

(72) Inventors: Sofia Ekstedt, Gothenburg (SE); Caj Hanson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/912,213

(22) PCT Filed: Apr. 6, 2020

(86) PCT No.: PCT/SE2020/050355
§ 371 (c)(1),
(2) Date: Sep. 16, 2022

(87) PCT Pub. No.: WO2021/206591
PCT Pub. Date: Oct. 14, 2021

(65) Prior Publication Data
US 2023/0123896 A1 Apr. 20, 2023

(51) Int. Cl.
*A61F 13/15* (2006.01)
*B32B 38/00* (2006.01)
(Continued)

(52) U.S. Cl.
CPC .. *A61F 13/15739* (2013.01); *A61F 13/15723* (2013.01); *B26D 7/1863* (2013.01); *B26F 1/384* (2013.01); *B32B 38/0004* (2013.01)

(58) Field of Classification Search
CPC .......... A61F 13/15739; A61F 13/15723; A61F 13/15747; B26D 7/1863; B26F 1/384; B32B 38/0004
See application file for complete search history.

(56) References Cited

U.S. PATENT DOCUMENTS

| 4,767,487 A | * | 8/1988 | Tomsovic, Jr. | ...... B65G 47/848 |
| | | | | 156/256 |
| 5,415,716 A | | 5/1995 | Kendall | |

(Continued)

FOREIGN PATENT DOCUMENTS

| CN | 1209177 A | 2/1999 |
| CN | 105473475 A | 4/2016 |

(Continued)

OTHER PUBLICATIONS

International Search Report & Written Opinion for International Application No. PCT/SE2020/050355; International Filing Date: Apr. 6, 2020; dated Oct. 29, 2020; 10 pages.

(Continued)

*Primary Examiner* — George R Koch
*Assistant Examiner* — Christopher C Caillouet
(74) *Attorney, Agent, or Firm* — CANTOR COLBURN LLP

(57) ABSTRACT

Disclosed is a method for transferring cut-out nonwoven material members, the method including feeding a continuous web of a nonwoven material towards cutter and anvil roll, passing the continuous web between the cutter and anvil roll, the cutter roll having knives protruding from the circumferential surface, the knives having an edge with a first outline shape seen in a circumferential direction of the cutter roll, cutting the continuous web thereby forming cut-out nonwoven material members having a second outline shape corresponding to the first outline shape of the respective edge of the knives, and transferring the cut-out members to a vacuum roll having an outer circumferential surface that includes a plurality of vacuum ports arranged in a pattern, the pattern including pattern units each having a third outline shape, the pattern units fitting within the second outline shape of the cut-out members.

11 Claims, 2 Drawing Sheets

(51) Int. Cl.
   *B26D 7/18* (2006.01)
   *B26F 1/38* (2006.01)

(56) References Cited

U.S. PATENT DOCUMENTS

| | | | |
|---|---|---|---|
| 5,826,475 | A | 10/1998 | Mysliwiec |
| 6,520,236 | B1 * | 2/2003 | Rajala ............... A61F 13/15772 |
| | | | 156/364 |
| 2007/0135787 | A1 | 6/2007 | Raidel et al. |
| 2012/0157282 | A1 * | 6/2012 | Schneider ............. A61F 13/496 |
| | | | 493/379 |
| 2015/0068372 | A1 | 3/2015 | Abney et al. |
| 2019/0328588 | A1 * | 10/2019 | Saevecke .......... A61F 13/53713 |

FOREIGN PATENT DOCUMENTS

| | | |
|---|---|---|
| CN | 109642375 B | 6/2022 |
| EP | 3626216 B1 | 6/2022 |
| WO | 0187561 A2 | 11/2001 |
| WO | 2013089009 A1 | 6/2013 |

OTHER PUBLICATIONS

Chinese Application No. 202080097271.7; Office Action with English Translation dated May 15, 2023; 9 pages.

* cited by examiner

METHOD FOR TRANSFERRING ONE OR MORE CUT-OUT NONWOVEN MATERIAL MEMBERS FOR USE IN AN ABSORBENT ARTICLE

CROSS REFERENCE TO RELATED APPLICATIONS

This application is a National Stage Application of PCT/SE2020/050355, filed Apr. 6, 2020, which is incorporated by reference in its entirety herein.

TECHNICAL FIELD

The present disclosure pertains to a method for transferring one or more cut-out nonwoven material members for use in an absorbent article. More specifically, the present disclosure pertains to a method for transferring one or more cut-out Carded Air Through bonded, Carded Spunlace or a Carded Needle punched nonwoven material members for use in an absorbent article.

BACKGROUND OF THE INVENTION

Absorbent articles such as diapers, sanitary pads, and incontinence pads may employ nonwoven material layers, such as layers of Carded Air Through bonded nonwoven materials, Carded Spunlace and Carded Needle punched nonwoven materials, as components in the absorbent articles. Such nonwoven materials are highly porous, air permeable and bulky structures, which may be desired for numerous reasons. For example, such permeable material layers may advantageously form part of a liquid receiving body in an absorbent article, e.g. be used between the topsheet and the absorbent core for acquisition and distribution of liquid to an absorbent core.

During production of absorbent articles, individual pieces of material may be cut out from continuous material layers in a cutting station including a rotating cutter roll and an anvil roll. The pieces may be cut to provide particular shaped configurations, such as for example hourglass shapes. After cutting and thereby forming individual material members, the individual cut-out members may be transferred from the cutting station by means of a perforated vacuum transfer roll while, eventual trim waste material may be separated from the cut-out material members. For highly porous and air permeable structures, the suction power of the transfer roll may cause an insufficient sub-pressure to maintain control of the cut-out material members during transfer of the members. This may be even more difficult if there are parts in the material or fibers that are not properly cut. If the cut-out material members are not properly transferred to the vacuum transfer roll, there is a risk that material members are discarded together with the trim material, are folded improperly creating defective end products or cause interruptions in the production. Such waste or defective products will increase the cost to manufacture the absorbent article as will interruptions in production lines. Absorbent articles are produced in high-speed production systems, interruptions and creation of increased waste in such production lines are costly.

It is therefore an object of the present invention to offer improvements in the method for producing one or more cut-out permeable material members and reduce the amount of defective products resulting from the production.

SUMMARY OF THE INVENTION

One or more of the above objects may be achieved with a method for transferring one or more cut-out nonwoven material members, the nonwoven material members being a Carded Air Through Bonded, Carded Spunlace and/or Carded Needle punched nonwoven material members, for use in an absorbent article in accordance with claim 1. Further embodiments are set out in the dependent claims, in the following description and in the drawings.

The present disclosure relates to a method for transferring one or more cut-out nonwoven material member(s), the nonwoven being Carded Air Through Bonded, Carded Spunlace and/or Carded Needle punched nonwoven material member(s), for use in an absorbent article, from a cutting station wherein the method including the step of;

a) feeding a continuous web of a nonwoven material, the nonwoven material being a Carded Air Through Bonded, Carded Spunlace and/or Carded Needle punched nonwoven material, in a machine direction towards a cutting station including a rotating cutter roll having an outer circumferential surface and an anvil roll;

b) passing the continuous web of nonwoven material in a nip formed between the rotating cutter roll and the anvil roll, the rotating cutter roll having one or more knives protruding from the outer circumferential surface, the one or more knives each having a cutting edge with a first outline shape;

c) cutting out one or more cut-out nonwoven material members from the continuous web of nonwoven material by passing the continuous web of nonwoven material between the rotating cutter roll and the anvil roll, the one or more cut-out nonwoven material members each having a second outline shape corresponding to the first outline shape of the respective cutting edge of the one or more knives; and d) transferring the one or more cut-out nonwoven material members from the cutting station to a vacuum transfer roll having an outer circumferential surface, the outer circumferential surface of the vacuum transfer roll including a plurality of vacuum ports arranged in one or more vacuum port pattern units each having a third outline shape, the one or more vacuum port pattern units fitting within the second outline shape of the one or more cut-out nonwoven material members.

The outline shape of the cut-out nonwoven material member may be any desired shape, such as for example an hourglass shape, a round shape, a rectangular shape or an oval shape. With "cut-out" is meant that the nonwoven material member is cut from a continuous material web to an individual nonwoven material member.

The nonwoven material according to the present disclosure is a carded nonwoven material. Carding is a process for making fibrous webs in which the fibres are aligned essentially parallel to each other in the direction in which the machine produces the web (machine direction). The carded nonwoven material according the present disclosure is bonded to provide fabric integrity by one of the following techniques; Air Through Bonding, Needlepunching or hydroentaglement (spunlaced nonwoven material).

Air Through Bonding is a thermal bonding that involved the application of heated air to the surface of the nonwoven fabric. The Through Air thermal bonding makes bulkier products by the overall bonding of a web container low melting fibers. This takes place in a carefully controlled hot air stream.

Needlepunching is a mechanical binding of the nonwoven web to form a nonwoven material fabric by puncturing the web with an array of barbed needles that carry tufts of the web's own fibres in a vertical direction through the web.

Spunlaced nonwoven material is a product of the bonding process of hydroentangling a web. Hydroentangling is a method of bonding a web of fibers or filaments by entangling them by using high-pressure water jets. A preformed web is entangled by means of high pressure, columnar water jets. As the jets penetrate the web, fibre segments are carried by the highly turbulent fluid and become entangled on a semi-micro scale. In addition to bonding the web, which needs little or no additional binder, the process can also be used to impart a pattern to the web.

Carded Air Through Bonded, Carded Spunlace and Carded Needle punched nonwoven materials are difficult to cut due to their highly porous and air permeable structure. If the material is not properly cut, the cut-out Carded Air Through Bonded, Carded Spunlace and/or Carded Needle punched nonwoven material members may not be completely separated from the trim waste or alternatively from an adjacent material member in the cutting step. This may lead to that cut-out material members are discarded together with trim material upon pulling away of the trim material and transferring of the cut-out material members from the cutting station to the vacuum transfer roll. If adjacent material members are not correctly separated it may also lead to defect products and/or interruption in the production. It may be sufficient that two or three fibers remain uncut for the separation problem to occur. Thus, it is of particular importance for these types of nonwoven materials that the suction force acting on the cut-out material members is sufficiently strong to overcome the cohesive forces of uncut fibers.

Furthermore, when using such highly porous and bulky structures as Carded Air Through Bonded, Carded Spunlace and/or Carded Needle punched nonwoven materials, the suction power of the vacuum transfer roll may cause an insufficient sub-pressure to maintain control of the material members during transfer of the cut-out high-loft material and separate from the trim waste material or from adjacent material members. If the cut-out nonwoven material members are not properly transferred to the vacuum transfer roll, there is a risk that the cut-out material members are improperly folded leading to quality problems and/or discarding of the products, or that the cut-out material members are discarded together with eventual trim material. Such waste may cause interruptions in production and assembly lines and will increase the cost to manufacture the absorbent article.

Conventional vacuum transfer rolls are provided with a homogenous vacuum port pattern extending over the entire circumferential surface of the vacuum transfer roll or in a continuous track pattern of vacuum port extending along the circumference of the vacuum transfer roll.

It has been found by the present inventors that when distributing the vacuum ports only over the outer circumferential surface in a vacuum port pattern which will fit within the outline shape of the cut-out nonwoven material members, the suction force applied to the cut-out nonwoven material members increases. In this way a more reliable and stable process is provided wherein the cut-out nonwoven material members are correctly transferred to the transfer roll, separated from the trim waste or adjacent members and properly kept on the vacuum transfer roll.

The term "absorbent article" refers to products that are placed against the skin of a wearer to absorb and contain body exudates, like urine, faeces and menstrual fluid such as for example a sanitary pad, a panty liner, an incontinence pad or a diaper. The invention furthermore refers to disposable absorbent articles, which means articles that are not intended to be laundered or otherwise restored or reused as an absorbent article after use.

The nonwoven material according to the present disclosure is a Carded Air Through Bonded, a Carded Spunlace or a Carded Needle punched nonwoven material or a combination thereof, such as a laminate thereof. The cut-out nonwoven material member may be a Carded Air through bonded nonwoven including staple fibers. The staple fibers may be natural fibers or cut lengths from manmade filaments, staple fibers are typically between 3 and 20 cm in length.

The Carded Air Through Bonded, Carded Spunlace and/or Carded Needle punched nonwoven material may have a basis weight within the range of from 20 gsm to 80 gsm. For such highly porous and air permeable nonwoven materials, the suction power of the vacuum transfer roll may be insufficient to pull and completely separate the cut-out nonwoven material members from the trim material or from adjacent nonwoven material members after the cutting step, thereby causing interruptions in the process, increased waste and defect products.

It has however been found by the present inventors that by distributing the vacuum ports only within areas of the outer circumferential surface of the vacuum transfer roll being arranged to face and coincide with the cut-out nonwoven material members upon transfer of the members to the vacuum transfer roll, the suction power applied to the respective cut-out nonwoven material member is increased, providing a stable and proper transfer and separation of the cut-out nonwoven material members from the trim waste.

The fibers in the nonwoven material may have a fiber denier within the range of from 3 to 10 dtex, optionally from 4 to 9 dtex.

The one or more vacuum port pattern units in the outer circumferential surface of the vacuum transfer roll may be, at least partly, matching with the outer contour of the outline shape of the one or more cut-out nonwoven material members. The one or more vacuum port pattern units may be matching with and distributed along the entire outer contour of the one or more cut-out nonwoven material members. The vacuum ports may alternatively be distributed only along parts of the outline shape of the one or more cut-out nonwoven material members, for example along at least 30%, such as at least 50%, such as from 60% to 100% of the outline shape of the one or more cut-out nonwoven material members, i.e. such that a section, of for example at least 30%, of the outline shape of the vacuum port pattern is free from vacuum ports. The one or more vacuum port pattern units may be matching with and at least distributed along a leading end section of the one or more cut-out nonwoven material members, as seen in the machine direction.

A total area of the vacuum ports of the respective vacuum port pattern units in the vacuum transfer roll outer circumferential surface may correspond to from 10% to 30% of the area of the one or more cut-out nonwoven material members, such that the total area of the vacuum ports corresponds to the area of the cut-out nonwoven material member applied on the vacuum port pattern unit of the vacuum transfer roll.

The number of vacuum ports may be higher within a leading half section of each of the third outline shape of the respective vacuum port pattern units than within a trailing half section of each of the third outline shape of the respective vacuum port pattern units, as seen in the machine direction. When transferring the cut-out nonwoven material members, it has been found to be more important to apply a higher suction force to the leading end of cut-out nonwoven material members than to the trailing end of the cut-out nonwoven material members. Hence, to distribute a higher number of vacuum ports in a leading end of the vacuum port pattern units increases the suction power in the parts where it is most desirable, leading to a decrease the interruption in the process and the number of defect products. The vacuum ports may thus be arranged with a greater distance to adjacent vacuum ports in a trailing half section of each of the third outline shape.

The vacuum pressure applied to the one or more cut-out nonwoven material members may be higher in a leading half section than in a trailing half section.

The vacuum port pattern may including a plurality of discrete vacuum port pattern units, arranged repeatedly in the outer circumferential surface and as seen in the circumferential direction of the vacuum transfer roll. The vacuum port pattern units may be arranged with the same distance between adjacent vacuum port pattern units or with varying distance between the adjacent vacuum port pattern units, as seen in the circumferential direction of the vacuum transfer roll.

The outer circumferential surface of the vacuum transfer roll which is outboard the vacuum port pattern units may thus be free from vacuum ports.

The anvil roll may rotate at a first rotational speed and the vacuum transfer roll may rotates at a second rotational speed, and the first rotational speed and second rotational speed may synchronized such that upon transfer of the one or more cut-out nonwoven material members to the vacuum transfer roll, the one or more vacuum port pattern units will each coincide with one of the one or more cut-out nonwoven material members.

The method according to the present invention may be included in a method for producing an absorbent article, such as for example a diaper, an incontinence pad or a sanitary napkin.

The method may include the step of applying the cut-out nonwoven material between a topsheet and a backsheet and sealing the outer edges of the topsheet and the backsheet, thereby assembling a disposable absorbent article. The cut-out nonwoven material may alternatively or additionally constitute the topsheet of the absorbent article.

The liquid permeable topsheet can be any suitable topsheet material as known by the person skilled in the art and may be fibrous topsheet material composed of a nonwoven material, e.g. spunbonded, meltblown, carded, hydroentangled, wetlaid etc.

Suitable nonwoven materials can be composed of natural fibers, such as wood pulp or cotton fibres, synthetic thermoplastic fibres, such as polyolefins, polyesters, polyamides and blends and combinations thereof or from a mixture of natural and synthetic fibres. Further examples of topsheet materials are porous foams. The materials suited as topsheet materials should be soft and non-irritating to the skin and be readily penetrated by body fluid, such as urine or menstrual fluid. The topsheet material may essentially constitute of non-absorbent fibers, such as synthetic thermoplastic fibers, such as such as polyolefins, polyesters, polyamides and blends and combinations thereof. The synthetic fibers may be monocomponent fibers, bicomponent fibers or multicomponent fibers including polyesters, polyamides and/or polyolefins such as polypropylene and polyethylene.

The backsheet may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. The backsheet material can be breathable so as to allow vapor to escape from the absorbent structure, while still preventing liquids from passing through the backsheet material.

BRIEF DESCRIPTION OF THE DRAWINGS

The present invention will be further explained hereinafter by means of non-limiting examples and with reference to the appended drawings wherein.

DETAILED DESCRIPTION

Figure 1:
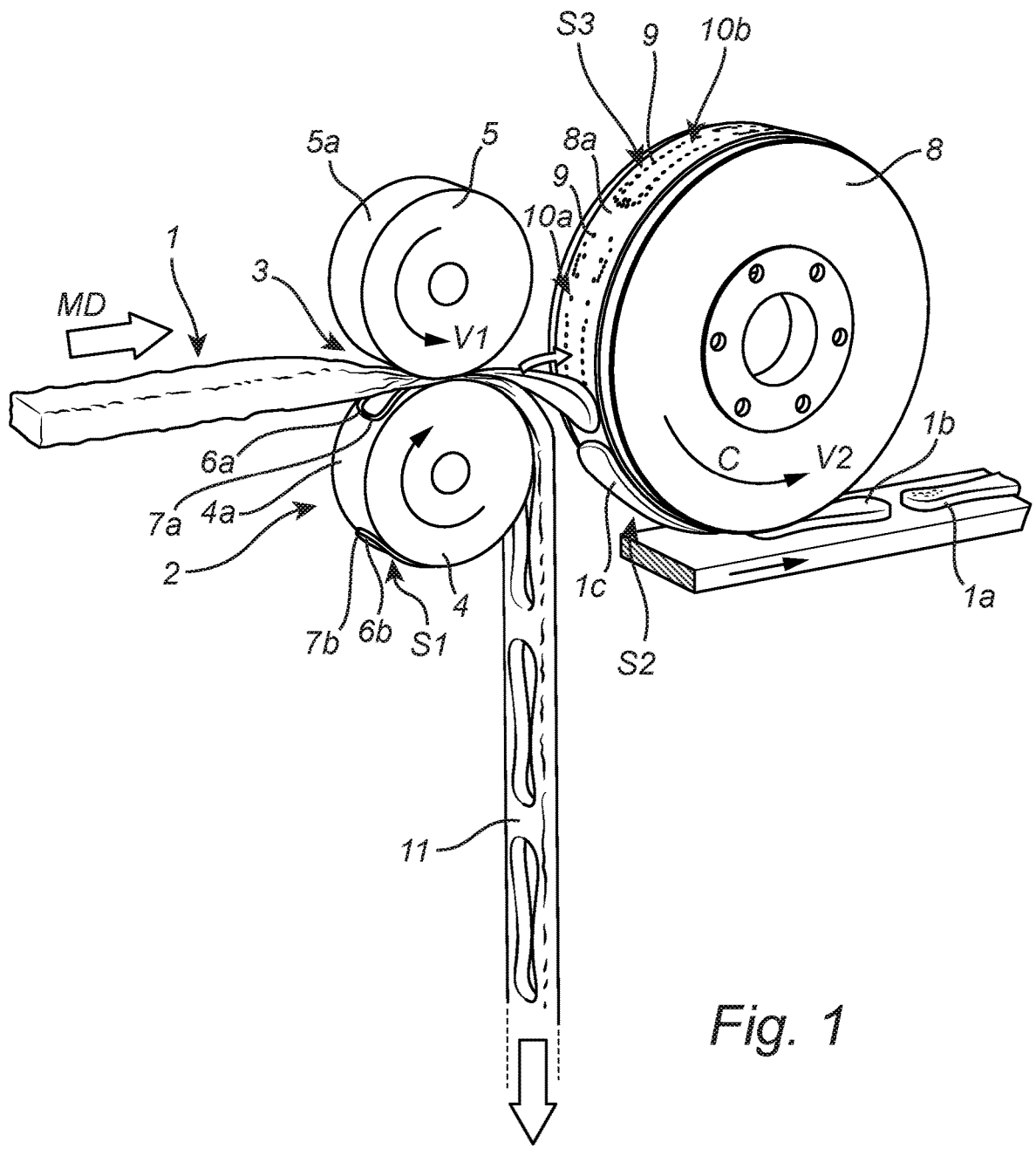
FIG. 1 shows schematically a method for transfer cut-out nonwoven material members.

It is to be understood that the drawings are schematic and that individual components, such as the material and the respective rolls are not necessarily drawn to scale. The cutting roll, anvil roll and the transport vacuum transport roll may also be differently arranged in relation to each other than in the drawings.

With reference to FIG. 1, a method of transferring cut-out nonwoven material members 1a, 1b, 1c from a cutting station 2 is schematically shown. The cut-out nonwoven material members are Carded Air Through Bonded nonwoven material members, Carded Spunlace nonwoven material members or Carded Needle punched nonwoven material members.

In a first step a continuous web of a Carded Air Through Bonded, a Carded Spunlace or a Carded Needle punched nonwoven material 1 is fed in a machine direction MD and towards the cutting station 2. The cutting station 2 includes a rotating cutter roll 4 with a circumferential outer surface 4a and a rotating anvil roll 5 with a smooth circumferential outer surface 5a. The continuous web of nonwoven material 1 is passed in a nip 3 formed between the rotating cutter roll 4 and the anvil roll 5. The rotating cutter roll 4 includes knives 6a, 6b protruding from the outer circumferential surface 4a of the cutter roll 4. The knives 6a, 6b each has a cutting edge 7a, 7b with a first outline shape S1.

In the cutting station 2, individual nonwoven material members 1a, 1b, 1c are cut out from the continuous web of nonwoven material 1 by passing the continuous web 1 between the rotating cutter roll 4 and the anvil roll 5. The resulting nonwoven material member 1a, 1b, 1c each has a second outline shape S2 corresponding to the first outline shape S1 of the respective cutting edge 7a, 7b of the one or more knives 6a, 6b. The respective cutting edge 7a, 7b may each have the same outline shape S1. After cutting of the continuous web of nonwoven material 1 in the cutting station 2, the cut-out nonwoven material members 1a, 1b, 1c are separated from the trim waste 11 and transferred from the cutting station 2 to a vacuum transfer roll 8. The trim waste resulting from the cutting station may for example be pulled away from the cut-out nonwoven material members 1a, 1b, 1c by means of vacuum.

To synchronize the cutting station 2 with the vacuum transfer roll 8, the cutter roll 4 and the anvil roll 5 rotates at a first rotational speed V1 and the vacuum transfer roll 8 rotates at a second rotational speed V2, and wherein the first rotational speed V1 and second rotational speed V2 are synchronized such that upon transfer of the one or more cut-out nonwoven material members 1a, 1b, 1c to the vacuum transfer roll 8, the one or more vacuum port pattern units 10a,10b will each coincide with one of the one or more cut-out nonwoven material members 1a, 1b, 1c.

The vacuum transfer roll 8 has an outer circumferential surface 8a including a plurality of vacuum ports 9. The vacuum ports 9 are arranged in one or more vacuum port pattern units 10a, 10b, 10c. The vacuum port pattern units 10a,10b each has a third outline shape S3 matching with the outer contour of the second outline shape S2 of the one or more cut-out nonwoven material members 1a,1b.

Figures 2, 3:
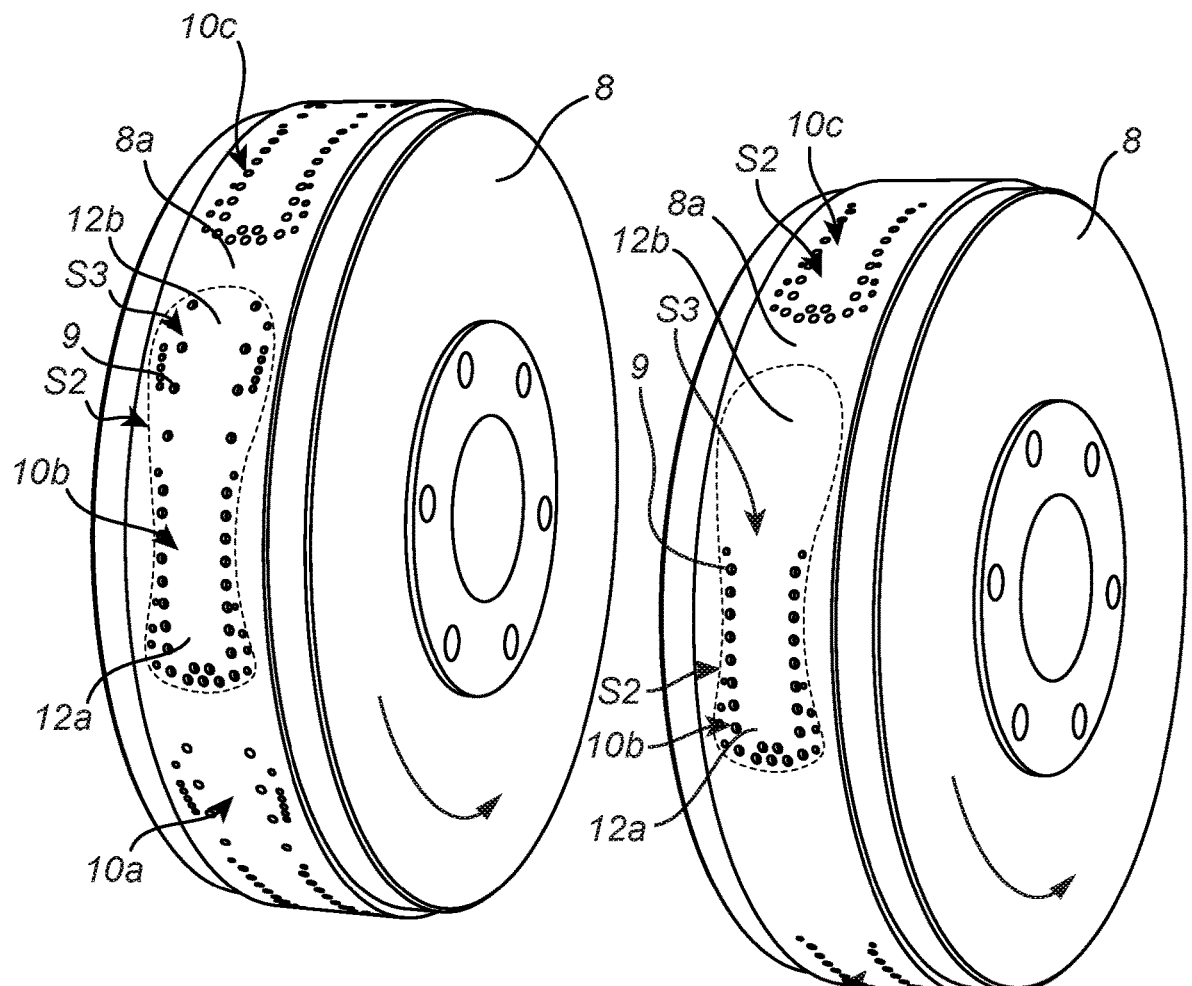
FIG. 2 illustrates a vacuum transfer roll according to the present invention.
FIG. 3 illustrates an alternative vacuum transfer roll according to the present invention.

As illustrated in FIG. 1, and which may also be seen in FIGS. 2 and 3, a total area of the vacuum ports 9 of the respective vacuum port pattern units 10a, 10b, 10c in the vacuum transfer roll outer circumferential surface 8a corresponds to from 10% to 30% of the area of a respective of the one or more cut-out nonwoven material members 1a, 1b, 1c when being transferred to the vacuum transfer roll. In the vacuum transfer roll 8 illustrated in FIGS. 1-3, the number of vacuum ports 9 is higher in a leading half section 12a of each of the third outline shape S3 of the respective vacuum port pattern units 10a, 10b, 10c than in a trailing half section 12b of each of the third outline shape S3 of the respective vacuum port pattern units 10a, 10b, 10c, as seen in the machine direction MD.

The leading half section 12a has a higher number of vacuum ports 9 and a greater open area than the trailing half section 12b, therefore the vacuum pressure applied to the one or more cut-out nonwoven material members 1a, 1b, 1c is higher in the leading half section 12a of the cut-out nonwoven material members 1a, 1b, 1c than to the trailing half section 12b thereof.

In FIG. 2, the vacuum transfer roll 8 is provided with vacuum port pattern units 10a, 10b, 10c each having a third outline shape S3 matching with second outline shape S2 of the one or more cut-out nonwoven material members 1a, 1b, 1c (shown in FIG. 1 and illustrated with a dotted contour line). In the leading half section 12a of the second outline shape S2 the number of vacuum ports 9 are higher than in the trailing half section 12b. The ports 9 are also distributed along the entire contour of the leading half section 12a and only along parts of the contour in the trailing half section 12b, or at least with a greater distance between adjacent points in the trailing half section 12b.

In FIG. 3, the vacuum transfer roll 8 is provided with vacuum port pattern units 10a, 10b, 10c each having a third outline shape S3 matching with second outline shape S2 in the leading half sections 12a. The trailing half sections 12b of the respective vacuum port pattern units 10a, 10b, 10c are free from vacuum ports 9.

The invention claimed is:

1. A method for transferring one or more cut-out nonwoven material members, the nonwoven material member(s) being a Carded Air Through Bonded, a Carded Spunlace and/or a Carded Needle punched nonwoven material member(s), for use in an absorbent article, from a cutting station, the method comprising:
   a) feeding a continuous web of a nonwoven material, the nonwoven material being a Carded Air Through Bonded, a Carded Spunlace and/or a Carded Needle punched nonwoven material, in a machine direction (MD) towards a cutting station including a rotating cutter roll having an outer circumferential surface and an anvil roll;
   b) passing the continuous web of nonwoven material in a nip formed between the rotating cutter roll and the anvil roll, the rotating cutter roll having one or more knives protruding from the outer circumferential surface of the cutter roll, the one or more knives each having a cutting edge with a first outline shape, as seen in a circumferential direction (C) of the rotating cutter roll;
   c) cutting out one or more cut-out nonwoven material members from the continuous web of nonwoven material by passing the continuous web of nonwoven material between the rotating cutter roll and the anvil roll, the one or more cut-out nonwoven material members each having a second outline shape (S2) corresponding to the first outline shape (S1) of the respective cutting edge of the one or more knives; and
   d) transferring the one or more cut-out nonwoven material members from the cutting station to a vacuum transfer roll having an outer circumferential surface, the outer circumferential surface of the vacuum transfer roll including a plurality of vacuum ports arranged in one or more vacuum port pattern units each having a third outline shape, the one or more vacuum port pattern units fitting within the second outline shape of the one or more cut-out nonwoven material members;
   wherein the plurality of vacuum ports are non-uniformly spaced between a leading half section and a trailing half section of each of the third outline shape of the respective vacuum port pattern units, as seen in the machine direction (MD).

2. The method for transferring one or more cut-out nonwoven material member according to claim 1, wherein the nonwoven material is a carded air through bonded nonwoven including staple fibers.

3. The method for transferring one or more cut-out nonwoven material member according to claim 1, wherein the nonwoven material has a basis weight within the range of from 20 gsm to 80 gsm.

4. The method for transferring one or more cut-out nonwoven material member according to claim 1, wherein the fibers in the nonwoven material have a fiber denier within the range of from 3 to 10 dtex.

5. The method for transferring one or more cut-out nonwoven material member according claim 1, wherein the one or more vacuum port pattern units in the outer circumferential surface of the vacuum transfer roll is at least partly matching with the outline shape of the one or more cut-out nonwoven material members.

6. The method for transferring one or more cut-out nonwoven material member according to claim 5, wherein the vacuum ports are distributed along from 30% to 100% of the outline shape of the one or more cut-out nonwoven material members.

7. The method for transferring one or more cut-out nonwoven material member according to claim 1, wherein a total area of the vacuum ports of the respective vacuum port pattern units in the vacuum transfer roll outer circumferential surface corresponds to from 10% to 30% of an area of a respective one or more cut-out nonwoven material members.

8. The method for transferring one or more cut-out nonwoven material member according to claim 1, wherein the number of vacuum ports is higher in the leading half section of each of the third outline shape of the respective vacuum port pattern units than in the trailing half section of each of the third outline shape of the respective vacuum port pattern units, as seen in the machine direction (MD).

9. The method for transferring one or more cut-out nonwoven material member according to claim 1, wherein the vacuum pressure applied to the one or more cut-out nonwoven material members is higher in the leading half section of the one or more cut-out nonwoven material members than to the trailing half section thereof.

10. The method for transferring one or more cut-out nonwoven material member (1*a*, 1*b*, 1*c*) according to claim 1, wherein the one or more vacuum port pattern units (10*a*,10*b*,10*c*) comprises a plurality of discrete vacuum port pattern units (10*a*,10*b*,10*c*), arranged repeatedly in the outer circumferential surface (8*a*) in the circumferential direction (C) of the vacuum transfer roll (8).

11. The method for transferring one or more cut-out nonwoven material member according to claim 1, wherein the anvil roll rotates at a first rotational speed and the vacuum transfer roll rotates at a second rotational speed, and wherein the first rotational speed and second rotational speed are synchronized such that upon transfer of the one or more cut-out nonwoven material members to the vacuum transfer roll, the one or more vacuum port pattern units will each coincide with one of the one or more cut-out nonwoven material members.

\* \* \* \* \*